(12) United States Patent
Hack et al.

(10) Patent No.: US 8,361,627 B2
(45) Date of Patent: Jan. 29, 2013

(54) ANTI-CORROSION LAYER FOR ALUMINUM AND MAGNESIUM ALLOYS

(75) Inventors: Theo Hack, Höhenkirchen (DE); Dominik Raps, Münich (DE); Ralf Supplit, Vienna (AT); Ulrich Schubert, Wöllersdorf (AT)

(73) Assignees: EADS Deutschland GmbH (DE); Technische Universität Wien (AT)

( * ) Notice: Subject to any disclaimer, the term of this patent is extended or adjusted under 35 U.S.C. 154(b) by 0 days.

(21) Appl. No.: 13/145,154

(22) PCT Filed: Jan. 7, 2010

(86) PCT No.: PCT/EP2010/050090
§ 371 (c)(1),
(2), (4) Date: Sep. 19, 2011

(87) PCT Pub. No.: WO2010/081757
PCT Pub. Date: Jul. 22, 2010

(65) Prior Publication Data
US 2012/0021232 A1    Jan. 26, 2012

(30) Foreign Application Priority Data
Jan. 19, 2009  (DE) .................. 10 2009 005 105

(51) Int. Cl.
*B32B 15/04*  (2006.01)
*B05D 3/00*   (2006.01)
*C09D 5/08*   (2006.01)

(52) U.S. Cl. .................. 428/450; 106/14.12; 106/14.15; 106/14.16; 106/287.11; 427/376.2; 427/419.2; 556/407

(58) Field of Classification Search ............... 106/14.12, 106/14.15, 14.16, 287.11; 427/376.2, 419.2; 428/450; 556/407
See application file for complete search history.

(56) References Cited

U.S. PATENT DOCUMENTS

| | | |
|---|---|---|
| 4,618,688 A | 10/1986 | DePasquale et al. |
| 5,200,237 A | 4/1993 | Sugama |
| 5,814,137 A | 9/1998 | Blohowiak et al. |
| 6,777,094 B2 | 8/2004 | Ostrovsky |
| 7,011,719 B2 | 3/2006 | Ostrovsky |

FOREIGN PATENT DOCUMENTS

| | | |
|---|---|---|
| EP | 0526847 A1 | 2/1993 |
| EP | 1887025 A1 | 2/2008 |
| JP | 2008133334 A | 6/2008 |
| WO | 2006129695 A1 | 12/2006 |

OTHER PUBLICATIONS

Khramov et al. Thin Solid Films, 2006, 514, pp. 174-181.
Zheludkevich et al. Chem. Mater, 2007, 19, pp. 402-411.
Phani et al. Surface & Coatings Technology, 2006, 201, pp. 3299-3306.
Vreugdenhil et al. J. Coat, Technical Articles, 2001, pp. 35-43.
Donley et al. Progress in Organic Coatings, 2003, 47, pp. 401-415.
Balbyshev et al. Progress in Organic Coatings, 2003, 47, pp. 337-341.
Khramov et al. Progress in Organic Coatings, 2003, 47, pp. 207-213.
Voevodin et al. Surface & Coatings Technology, 2006, 201, pp. 1080-1084.
Bedford et al. Synthesis 2005, No. 4, pp. 622-626.

*Primary Examiner* — D. S. Nakarani
(74) *Attorney, Agent, or Firm* — Lerner, David, Littenberg, Krumholz & Mentlik, LLP

(57) ABSTRACT

The invention relates to a composition for the corrosion protection of metal substrates and to the production thereof, and to a method for producing corrosion-resistant coatings.

14 Claims, 1 Drawing Sheet

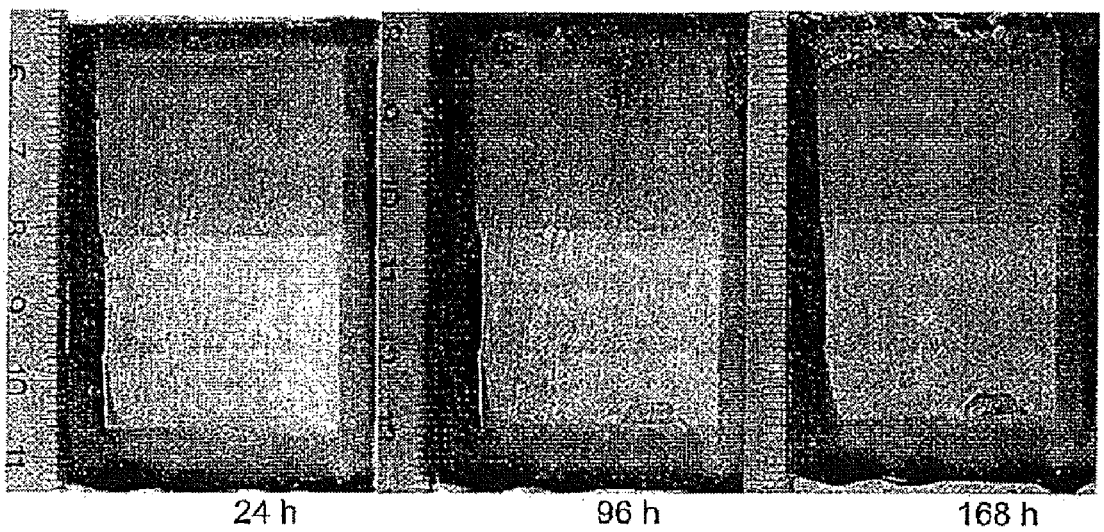

ANTI-CORROSION LAYER FOR ALUMINUM AND MAGNESIUM ALLOYS

CROSS-REFERENCE TO RELATED APPLICATIONS

This application is a national phase entry under 35 U.S.C. §371 of International Application No. PCT/EP2010/050090, filed Jan. 7, 2010, published in German, which claims the benefit of the filing date of German Patent Application No. 10 2009 005 105.8, filed Jan. 19, 2009, the entire disclosure of which is hereby incorporated herein by reference.

The invention relates to a composition for the corrosion protection of metal substrates and to the production thereof, and to a method for producing corrosion-resistant coatings.

Corrosion of a metal material leads to a change in the properties of the metal, which results in a reduction in quality and thus involves considerable impairments of the function of the material or of the technical system of which said material forms part. Signs of corrosion may appear in the material in the form of cracks, holes, cavities or planar reductions in wall thickness. Corrosion is caused, for example, by electrochemical or chemical reactions between the metal material and its environment and can also be triggered, inter alia, by the formation of condensation, high ambient humidity, seawater, or else by dirt and gas particles in the air such as $SO_2$, salts and hygroscopic dust or by residues of chlorides, sulfides, sulfates or acids.

Materials made of light metals such as magnesium and aluminum as well as alloys of these metals are currently being used increasingly in many branches of industry, in particular components made of magnesium, aluminum or corresponding alloys are increasingly used in automotive, aviation and aerospace industries since they enable high strength and low weight at the same time. However, it is precisely these materials which require particularly effective corrosion protection.

Varnishes and/or galvanically applied coatings which form a barrier between metal and the environment are generally used to protect metal materials against corrosion.

The anti-corrosion properties of magnesium and aluminum and alloys thereof can be improved, for example by anodizing. Other possibilities for improving the anti-corrosion properties of such materials consist in the application of chemical conversion coatings, for example by chromating or zinc-phosphating.

A further possibility for protecting metal materials against corrosion is offered by the sol-gel process. Protective sol-gel-based layers can be applied to the metal surface by simple coating methods such as dipping, centrifugation or spraying.

Anti-corrosion sol-gel layers for aluminum and titanium alloys which are based on $ZrO_2/SiO_2$ precursors are commercially available and are described, for example, in U.S. Pat. No. 5,814,137.

Sol-gel methods for use on magnesium alloys are known from U.S. Pat. Nos. 6,777,094 and 7,011,719. A further sol-gel system for use on magnesium alloys is described by Khramov et al. (Thin Solid Films 2006, 514, 174) and is based on tetraethoxysilane and phosphonatoethyltriethoxysilane. The phosphonate group reacts with the surface of the magnesium alloy and increases both the adhesion and the barrier effect of the coating. $ZrO_2/CeO_2$-based anti-corrosion sol-gel layers were described by Phani et al. (Mater. Corros. 2005, 56, 77).

A further approach, based on a self-assembling nanophase particles (SNAL) process, for protecting aluminum alloys against corrosion was published by Vreugdenhil et al. (J. Coat. Technol. 2001, 56, 77).

A sol-gel coating which additionally contains a corrosion-inhibiting substance which can be selectively released at the point of corrosion is described by Zheludkevich et al. (Chem. Mater. 2007, 19, 402). In this method silica gel nanoparticles which have been impregnated with the corrosion inhibitor benzotriazole are added to the sol-gel material. This inhibiting substance can be released when microdefects and greater damage are caused and can protect any unprotected metal surfaces or metal interfaces against corrosion.

A drawback of the aforementioned coating is often the low level of adhesion on the metal substrate or else the large layer thicknesses, which lead to undesired additional weights of the components, in particular in aircraft construction.

There is a need for anti-corrosion coatings which can be used with low layer thicknesses. There is a further need for such coatings which exhibit improved adhesion on the substrate.

An object of the present invention consists in the provision of a composition which improves the resistance against corrosion of a metal substrate.

A further object of the present invention consists in the provision of an anticorrosive coating with low layer thickness.

It is further desirable to achieve improved adhesion of the anticorrosive coating on a metal substrate.

It is also desirable to provide an anticorrosive coating which improves the adhesion of subsequent coatings.

A solution according to the invention consists in an anticorrosive composition which comprises a sol-gel material and at least one corrosion-inhibiting silane compound. The corrosion-inhibiting silane compound can be linked to the sol-gel network via covalent bonds and thus also further confers a stable coating, even if the anti-corrosion layer suffers mechanical damage. The covalent bonding of the corrosion-inhibiting substance to the sol-gel network also prevents any washing out or bleeding and ensures a uniform distribution.

In accordance with a further aspect of the present invention an anticorrosive silane compound is provided which can be incorporated into the network of a sol-gel coating.

In accordance with a further aspect of the present invention a method for producing an anticorrosive coating is provided as well as the use thereof to protect a metal substrate against corrosion. In accordance with a further aspect of the present invention a method for producing an anticorrosive protective coating is provided in which commercially available matrix materials can also optionally be used, which reduces the complexity of manufacture and thus reduces production costs.

FIG. 1 shows salt spray tests of metal substrates comprising an anticorrosive coating according to the present invention.

The term "corrosion" describes any change in the metal which leads to oxidation in the corresponding metal cation, wherein metal oxides, carbonates, sulfites, sulfates or else sulfides are generally formed which may optionally be hydrated.

Within the scope of the present invention a "corrosion-inhibiting substance" is a chemical substance which is able to reduce the rate of corrosion when present in sufficient concentration in a corrosive system.

Within the scope of the present invention "metal substrate" is to be understood to mean any substrate which consists thoroughly of metal or comprises a metal layer, at least on its surface.

Within the meaning of the present invention the term "metal" includes not only pure metals, but also mixtures of metals and metal alloys, these metals and metal alloys preferably being susceptible to corrosion.

The composition according to the invention can be applied to metal substrates which, for example, comprise a metal from the group of iron, aluminum, magnesium, zinc, silver and copper, although the field of application of the present invention is not limited to these metals. Metal alloys which can particularly benefit from the present invention include, for example, steel and brass as well as aluminum- and magnesium-containing alloys. In particular, the composition according to the invention is adapted to protect the light metals, which are particularly susceptible to corrosion, of magnesium and aluminum as well as the alloys thereof and to protect materials which contain these light metals.

Within the scope of the present invention an "anticorrosive composition" is to be understood to mean a mixture of compounds which can be used to produce an anticorrosive coating on a metal substrate. The term "anticorrosive coating" refers to the protective layer applied to and cured onto the metal substrate.

In accordance with the invention the anticorrosive composition comprises a sol-gel material, wherein the sol-gel material contains at least one corrosion-inhibiting silane compound. The anticorrosive composition may optionally comprise further, additional components.

Sol-Gel Material

Sol-gel materials are, for example, synthesized by means of hydrolysis of metal or metalloid alkoxides, in the case of alkoxy silane precursors with the use of an acid (for example HCl) or a base (for example $NH_3$) as a catalyst. A typical sol-gel process is described by the following three generalized reaction formulae:

(1) Hydrolysis

(2) Condensation

Alcohol condensation

Water condensation

in which M is a metal and Si and R are normally an alkyl group $(C_nH_{2n+1})$ or the like.

During the hydrolysis reaction the alkoxy groups (—OR) are replaced by hydroxyl groups (—OH). The condensation reaction then takes place, in which alcohol (ROH) or water ($H_2O$) is produced as a by-product.

Examples of suitable alkoxysilane compounds include tetraalkoxysilanes, aryltrialkoxysilanes, alkenyltrialkoxysilanes, glycidoxyalkyltrialkoxysilanes, aminoalkyltrialkoxysilanes and (meth) acryltrialkoxysilanes as well as mixtures thereof. Methyltrimethoxysilane, glycidoxypropyltrimethoxysilane, methacryloxypropyltrimethoxysilane and tetraethoxysilane as well as mixtures thereof are particularly preferred.

The properties of the coating, for example hardness, can be increased by adding silicon-free precursors. Examples include organometallic compounds such as tetra-iso-propoxy titanium, tri-iso-propoxy aluminum, tri-sec-butoxy aluminum, tetrabutoxy zirconium and tetrapropoxy zirconium.

Small particles such as nanoparticles of metal oxides, metal carbides and metal nitrides can additionally be added to the sol-gel matrix. Suitable materials include, for example, SiC, $Si_3N_4$, $Al_2O_3$, $ZrO_2$, $TiO_2$ or $SiO_2$. A small particle size increases dispersibility and thus enables layer defects to be remedied. For example, nanoparticles can increase the scratch-resistance of the anticorrosive coating, reinforce its barrier effect against corrosive media and improve the adhesion of primer or cover layer coatings. In order to increase compatibility with the sol-gel matrix, the particles may optionally be functionalized. Functionalization can occur, for example, by chemo-mechanical methods during the grinding of the particles. A compound suitable for the functionalization of nanoparticles is, for example, TODA (3,6,9-trioxadecanoic acid).

Further constituents which can be added to the sol-gel matrix include, for example, dyes or pigments for coloration.

The degree of cross-linking influences the mechanical properties of the coating. The mechanical properties can optionally be further adjusted by organofunctional silanes which are able to form an organic network in addition to an inorganic network. For example, non-cross-linking functional groups, such as alkyl or phenyl groups, can increase the flexibility of the system.

The sol-gel-forming components can be hydrolyzed by adding water.

The working properties of the sol-gel material can be adjusted by solvents and additives. For example, ethanol, isopropanol, 1-butanol, butoxyethanol, butyl acetate, isopropoxyethanol and glycol are suitable solvents. For example, the additives can comprise wetting agents, leveling agents, anti-foaming agents, dispersing aids, UV stabilizers and silicons as well as condensation catalysts such as acids or bases. The finished sol can also be provided with organic polymers in order to increase flexibility.

In accordance with one embodiment the sol-gel material is produced from methyltrimethoxysilane, tetraethoxysilane, ethanol and isopropanol, wherein hydrolysis occurs by adding water and 85% phosphoric acid.

In one embodiment the at least one corrosion-inhibiting silane compound is added to the finished sol-gel material and the mixture is stirred for several hours, for example for 1 to 8 hours, 2 to 6 hours or 4 hours. In another embodiment the at least one corrosion-inhibiting silane compound of the reaction mixture is added with the sol-gel-forming components before hydrolysis.

Preferred anticorrosive coatings exhibit excellent adhesion to the substrate. Ideally, this can be achieved in that the metal atoms of an underlying metal substrate form covalent bonds with the compounds of the sol-gel matrix, wherein Si—O—M bonds can be formed, for example in the case of silanes. If the sol-gel layer additionally contains non-siliceous components, covalent bonds can also be formed between these and the metal atoms.

Corrosion-Inhibiting Silane Compound

In accordance with the invention the anticorrosive composition comprises at least one corrosion-inhibiting silane compound.

In accordance with one embodiment the at least one corrosion-inhibiting silane compound has the general formula (I)

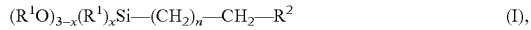

in which the substituents $R^1$ may be the same or different and are selected from the group comprising hydrogen, alkyl, alkenyl, alkynyl, acyl or aryl, the substituent $R^2$ is a nitrogen-containing, optionally substituted heterocyclic moiety, x is equal to 0, 1 or 2, and n is an integer $\geq 0$.

Alkyl moieties optionally comprise substituted, straight-chain, branched or cyclic moieties containing 1 to 20 carbon atoms, preferably 1 to 10 carbon atoms and in particular low alkyl moieties containing 1 to 6, preferably to 4 carbon atoms. Specific examples include methyl, ethyl, n-propyl, isopropyl, n-butyl, sec.-butyl, tert.-butyl, isobutyl, n-pentyl, n-hexyl, dodecyl, octadecyl and cyclohexyl.

Alkenyl and alkynyl moieties may optionally comprise substituted, straight-chain or branched moieties containing 1 to 20 carbon atoms, preferably 1 to 10 carbon atoms and, in particular, low alkyl moieties containing 1 to 6, preferably 1 to 4 carbon atoms. Specific examples of alkenyl moieties include allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl. Specific examples of alkynyl moieties include propynyl, but-2-yn-1-yl, but-3-yn-1-yl and 1-methyl-but-3-yn-1-yl.

Acyl moieties may optionally comprise substituted moieties of organic acids which are formally produced by cleaving an OH group from the organic acid, for example moieties of a carboxylic acid or moieties of acids derived therefrom such as thiocarboxylic acid, optionally n-substituted imino carboxylic acids or the moieties of carbonic acid monoesters, optionally n-substituted carbamic acids, sulfonic acids, sulfinic acids, phosphonic acids, phosphinic acids.

Aryl moieties can optionally comprise substituted mono-, bi- or polycyclic aromatic systems, for example phenyl, naphthyl, tetrahydronaphthyl, indenyl, indanyl, pentalenyl, fluorenyl and the like, preferably phenyl.

The substituents $R^1$ are preferably selected independently of one another from the group comprising hydrogen, alkyl, acyl or aryl. The substituents $R^1$ are more preferably selected independently of one another form the group comprising methyl, ethyl, n-propyl, isopropyl, n-butyl, sec.-butyl, tert.-butyl, isobutyl, n-pentyl, n-hexyl, dodecyl, octadecyl and cyclohexyl. Methyl is particularly preferred.

An example of suitable nitrogen-containing, heterocyclic moieties are azolyls. The substituent $R^2$ is preferably selected from the group consisting of tetrazolyls, triazolyls, pyrazolyls, imidazolyls, isoxazolyls, oxazolyls, isothiazolyls and thiazolyls.

Specific examples of tetrazolyls include 1H-, 2H- or 5H-tetrazolyl or 5-substituted tetrazolyls, such as 5-methyltetrazolyl or 5-phenyltetrazolyl. Specific examples of triazolyls include 1,2,3-triazolyl or 4- and/or 5-substituted 1,2,3-triazolyls, such as benzotriazolyl, 4-phenyl-1,2,3-triazolyl, 1,2-naphtotriazolyl, 5-methylbenzotriazolyl or 4-nitrobenzotriazolyl. Specific examples of pyrazolyls include pyrazolyl itself or 3-, 4- and/or 5-substituted pyrazolyls, such as 3,5-dimethylpyrazolyl, 6-nitroindazolyl, 4-benzylpyrazolyl, 4,5-dimethylpyrazolyl or 3-allylpyrazolyl. Specific examples of imidazolyls include imidazolyl itself or 2-, 4- and/or 5-substituted imidazolyls, such as adenyl, guanyl, benzimidazolyl, 5-methylbenzimidazolyl, 2-phenylimidazolyl, 2-benzylimidazolyl, 4-allylimidazolyl, 4-(β-hydroxyethyl)-imidazolyl, purinyl, 4-methylimidazolyl, xanthinyl, hypoxanthenyl, mercaptobenzimidazolyl or 2-methylimidazolyl. Specific examples of isoxazolyls include isoxazolyl itself or 3-, 4- and 7- or 5-substituted isoxazolyl, such as 3-mercaptoisoxazolyl, 3-mercaptobenzisoxazolyl or benzisoxazolyl. Specific examples of oxazolyls include oxazolyl itself or 2-, 4- and/or 5-substituted oxazolyls, such as 2-mercaptooxazolyl or 2-mercaptobenzoxazolyl. Specific examples of isothiazolyls include isothiazolyl itself or 3-, 4- and/or 5-substituted isothiazolyls, such as 3-mercaptoisothiazolyl, 3-mercaptobenzisothiazolyl or benzisothiazolyl. Specific examples of thiazolyls include thiazolyl itself or 2-, 4- and/or 5-substituted thiazolyls, such as 2-mercaptothiazolyl, 2-mercaptobenzothiazolyl or benzothiazolyl.

Other suitable nitrogen-containing heterocyclic moieties include, for example, pyridinyls, pyrimidinyls, quinolinyls or indolyls, which may optionally be further substituted.

In accordance with a further embodiment the at least one corrosion-inhibiting silane compound has the general formula (I)

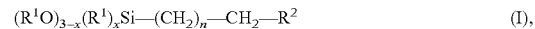

in which the substituents $R^1$ may be the same or different and are selected from the group comprising hydrogen, alkyl, acyl or aryl, (as defined herein), the substituent $R^2$ is an optionally substituted imidazolyl (as defined herein), x is equal to 0, 1 or 2, and n is an integer $\geq 0$.

The alkyl, alkenyl, alkynyl, acyl or aryl moieties and the nitrogen-containing heterocyclic moieties may optionally be substituted and, for example, carry one or more substituents from the group of halogens such as F, Cl and Br or acryloxy, amino, amide, aldehyde, alkoxy, alkoxycarbonyl, alkylcarbonyl, carboxy, cyano, epoxy, hydroxyl, keto, methacryloxy, mercapto, phosphoric acid, sulfonic acid or vinyl groups.

In accordance with one embodiment n is an integer between 0 and 10 or between 1 and 8. Preferably, n is an integer between 2 and 4.

The substituent $R^2$ is preferably attached to the $(R^1O)_{3-x}(R^1)_xSi-(CH_2)_n-CH_2$ moiety via a nitrogen atom. However, the substituent $R^2$ can also be linked to the $(R^1O)_{3-x}(R^1)_xSi-(CH_2)_n-CH_2$ moiety via another heteroatom or a C atom.

In one embodiment of the present invention the at least one corrosion-inhibiting silane compound is linked to the sol-gel network via covalent bonds. In accordance with another embodiment the at least one corrosion-inhibiting silane compound is not linked to the sol-gel network via covalent bonds.

The at least one corrosion-inhibiting silane compound is preferably selected from the group consisting of N-trimethoxysilylpropyl imidazole, 1N-trimethoxysilylpropyl-1,2,4-triazole and 4N-trimethoxysilylpropyl-1,2,4-triazole and mixtures thereof.

The inventors have found that the anticorrosive protective coating of the present invention is also adapted to protect materials against intercrystalline corrosion. This type of corrosion can occur in materials which form intermetal phases and is caused when the intermetal phases at the particle boundaries or edges close to particle boundaries have a considerably lower corrosion potential than the surrounding metal matrix. For example, intermetal phases can form in alloys of aluminum, magnesium and copper, wherein a predominant part of these intermetal phases can consist of S-phases which have a defined $Al_2MgCu$ composition. These phases are selectively dissolved at the start of the corrosion reaction, enriched with copper and then form a cathode relative to the surrounding metal matrix. In the case of an AlMgCu alloy, the corrosive attack on the S-phases thus begins with the dissolution of magnesium and aluminum. Owing to this dissolution process, copper is enriched locally at the edges of the dissolving S-phase regions, thus triggering further corrosion since the effective surface area of the cathodic zones increases. Without establishing a specific theory, the inventors believe that the corrosion-inhibiting silane compound can prevent corrosion of AlMgCu alloys by suppressing the dissolution of S-phases and the deposition of copper. For example, the nitrogen-containing group of the silane compound can be absorbed on metal centers of the intermetal phases and thus make it difficult for the metal constituents to dissolve away.

The at least one corrosion-inhibiting silane compound can be contained in the anticorrosive composition in an amount of 0.1 to 90% by weight based on the weight of the composition. The at least one corrosion-inhibiting silane compound is preferably contained in an amount of 0.2 to 80% by weight, 0.5 to 40% by weight, 1 to 20% by weight, 2 to 10% by weight or 3 to 5% by weight based on the weight of the composition.

In accordance with one embodiment the anticorrosive composition contains merely one corrosion-inhibiting silane compound. In accordance with another embodiment the anticorrosive composition contains a mixture of different corrosion-inhibiting silane compounds. In a specific embodiment the anticorrosive composition contains merely corrosion-inhibiting silane compounds which are linked to the sol-gel network via covalent bonds. In another specific embodiment the anticorrosive composition contains merely corrosion-inhibiting silane compounds which are not linked to the sol-gel network via covalent bonds. In a further specific embodiment the anticorrosive composition contains mixtures of corrosion-inhibiting silane compounds, some of which are linked to the sol-gel network via covalent bonds and some of which are not.

Additional, Optional Components

In addition to the sol-gel material which contains a corrosion-inhibiting silane compound, the anticorrosive composition may comprise additional optional components selected from the group comprising nanoparticles, dyes, solvents and additives (as defined herein).

For example, the anticorrosive composition can additionally comprise nanoparticles of metal oxides, metal carbides and metal nitrides. For example, suitable materials include SiC, $Si_3N_4$, $Al_2O_3$, $ZrO_2$, $TiO_2$ or $SiO_2$. The particles may optionally also be functionalized. Functionalization can occur, for example, by chemo-mechanical methods during the grinding of the particles. A compound suitable for the functionalization of nanoparticles is, for example, TODA (3,6,9-trioxadecanoic acid).

The working properties of the anticorrosive composition can be adjusted by solvents and additives. For example, ethanol, isopropanol, 1-butanol, butoxyethanol, butyl acetate, isopropoxyethanol and glycol are suitable solvents. For example, the additives can comprise wetting agents, leveling agents, anti-foaming agents, dispersing aids, UV stabilizers and silicons as well as condensation catalysts such as acids or bases.

In one embodiment the anticorrosive composition comprises, in addition to the sol-gel material which contains the at least one corrosion-inhibiting silane compound, at least one further corrosion-inhibiting non-silane compound. Within the meaning of the present invention a "corrosion-inhibiting non-silane compound" is a compound which exhibits a corrosion-inhibiting property, but does not contain any silicon-organic fractions. Examples of suitable corrosion-inhibiting non-silane compounds include organic, corrosion-inhibiting active ingredients, such as benzotriazole, 5-methylbenzotriazole, 2-mercaptothiazole, mercaptobenzimidazole, mercaptobenzothiazole, 8-hydroxyquinoline, succinic acid, 2-benzothiazolylthiosuccinic acid or zinc-5-nitroisophthalate, and inorganic corrosion-inhibiting active ingredients such as strontium aluminum tripolyphosphate or zinc phosphate.

The at least one corrosion-inhibiting non-silane compound may optionally be microencapsulated. Natural, semi-synthetic or synthetic materials can be used as encasing materials. Natural encasing materials include, for example, gum Arabic, agar-agar, agarose, maltodextrins, fats and fatty acids, cetyl alcohol, collagen, chitosan, lecithins, gelatin, albumin, shellac, polysaccharides, polypeptides, saccharose or waxes. Examples of semi-synthetic encasing materials include chemically modified celluloses, for example cellulose acetate, ethyl cellulose, hydroxypropyl cellulose, hydroxypropylmethyl cellulose and carboxymethyl cellulose or starch derivatives. For example, polymers such as polyacrylates, polyamides, polyurethanes or polyureas can be used as synthetic encasing materials.

Application of the Anticorrosive Composition

In accordance with the invention a method is provided for protecting a metal substrate against corrosion, said method comprising the provision of a metal substrate, the provision of an anticorrosive composition comprising a sol-gel material, the sol-gel material containing at least one corrosion-inhibiting silane compound, the application of the composition onto the substrate, and the curing of the composition.

The composition can be applied by means of conventional application methods, such as dipping, centrifugation, flow coating, brushing or spraying. The coating can be cured thermally, for example at a temperature between 60° C. and 180° C., preferably at approximately 120° C. The coating can alternatively or additionally also be cured by irradiation, for example with UV light, infrared or the like.

The coating is set to a layer thickness between 0.1 µm and 100 µm, preferably to a layer thickness between 0.2 µm and 50 µm or between 0.5 µm and 10 µm. In particular, the layer thickness is preferably between 1 µm and 5 µm or between 3 µm and 4 µm. Layer thickness and resistance to corrosion can optionally be increased further by multiple coating.

In one embodiment the substrate is pretreated before the application of the anticorrosive composition. In accordance with a specific embodiment the substrate is first cleaned and then etched or acid cleaned. Suitable media for cleaning include, for example, ethanol/surfactant mixtures or alkaline cleaning agents, such as Ardrox 6376 (Chemetall GmbH). The etching or acid cleaning of the substrate may be carried out, for example, with an aqueous solution which contains 5% by weight sodium nitrate in 20% by weight acetic acid or with commercially available etchants such as Ardrox 1277 or Gardoclean T5497 (Chemetall GmbH). In accordance with another embodiment the surface of the substrate is conditioned with a base after the acid cleaning step by dipping the substrate momentarily into an alkaline cleaning bath.

In accordance with one embodiment a cover layer, also known as a top coat, is additionally applied to the cured, anticorrosive coating. For example, polyurethane- or epoxy-based coatings are suitable as a cover layer. The cover layer preferably exhibits a high level of chemical resistance.

In accordance with another embodiment a base layer, also known as a primer, is additionally applied to the cured, anticorrosive coating (sol-gel layer). For example, an epoxy-based primer is suitable as a base layer.

EXAMPLES

Example 1

Production of Trimethoxysilylpropyl Imidazole 5 g (73 mmol) of imidazole were dissolved in 100 ml of tetrahydrofurane and 1.73 g (73 mmol) of sodium hydride were added. The suspension was stirred for 4 hours, after which 10 ml of iodopropyltrimethoxy silane (52 mmol) were added and the reaction mixture was heated under reflux for 18 hours. 15 ml of dichloromethane were then added and the reaction mixture was filtered. The filtrate was concentrated under reduced pressure and the product was distilled off at 150-155° C. at 8 mbar. The yield was 8.2 g (60%).

$^1$H-NMR (ppm, CDCl$_3$): 3.50 (s, 1), 0.49 (t, $^3$J=8 Hz, 2), 1.86 (m, 3), 4.09 (t, $^3$J=7 Hz, 4), 8.86-7.04 (m, 5-6), 7.37 (s, 7).

Example 2

Production of 1N- and 4N-trimethoxysilylpropyl-1,2,4-triazole 5 g (72 mmol) of 1,2,4-triazole were dissolved in 100 ml of absolute tetrahydrofurane and 1.73 g (72 mmol) of sodium hydride were added. The reaction mixture was stirred for 4 hours, after which 10 ml of iodopropyltrimethoxy silane (52 mmol) were added and the reaction mixture was heated under reflux for 18 hours. 20 ml of dichloromethane were then added and the reaction mixture was filtered. The solvent was removed at 150-155° C. under reduced pressure (8 mbar) and then filtered. The yield was 6.4 g (50%).

$^1$H-NMR (ppm, CDCl$_3$): 3.51 (s, 1), 0.52 (t, $^3$J=8 Hz, 2), 1.83 (m, 3), 4.09 (t, $^3$J=7 Hz, 4), 7.86 (s, 5), 8.01 (s, 5'), 8.11 (s, 5).

Example 3

Production of a Sol-Gel System 120 g of methyltriethoxysilane, 20 g of tetraethoxysilane, 30 g of ethanol and 12 g of isopropanol were placed in a closable vessel and a mixture of 0.154 g of phosphoric acid (85%) in 18 g of water was added dropwise with stirring. The solution was stirred at room temperature for 24 h and then stored at −20° C. for a maximum of three months.

Example 4

Production of an Anticorrosive Coating on a Mg AZ31 Substrate 1 ml of N-trimethoxysilylpropyl imidazole was added to 26 ml of the sol-gel system from Example 3 and the mixture was stirred for 4 hours.

The substrates formed of magnesium alloy AZ31 were degreased in an ethanol/surfactant mixture in an ultrasonic bath for 5 mins and then etched for one minute in an aqueous solution which contained 5% by weight of sodium nitrate in 20% by weight of acetic acid. The substrate was then cleaned in deionized water in an ultrasonic bath and dried in the open air.

The anticorrosive composition was applied by means of dip-coating at a dipping rate of 20 cm/min. The films obtained were dried for 30 mins at room temperature and hardened for one hour at 120° C.

In the hydrogen test in contact with 5% saline solution the substrates thus coated exhibited only a very low level of outgassing within a period of one week. The results of the salt spray test are shown in FIG. 1, wherein the left-hand image shows the state of the coating after 24 hours, the centre image after 96 hours and the right-hand image after 168 hours.

The invention claimed is:

1. An anticorrosive composition comprising a sol-gel material, wherein the sol-gel material comprises at least one corrosion-inhibiting silane compound, wherein the at least one corrosion-inhibiting silane compound has the general formula (I)

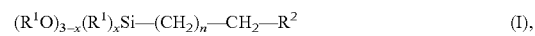

$(R^1O)_{3-x}(R^1)_xSi—(CH_2)_n—CH_2—R^2$ (I), in which the substituents $R^1$ may be the same or different and are selected from the group consisting of hydrogen, alkyl, acyl or aryl, the substituent $R^2$ is a nitrogen-containing, heterocyclic moiety, x is equal to 0, 1 or 2, and n is an integer between 0 and 10, wherein the substituent $R^2$ is selected from the group consisting of triazolyls, pyrazolyls, isoxazolyls, oxazolyls and thiazolyls.

2. The composition according to claim 1, wherein the alkyl moieties of the substituents $R^1$ are selected independently of one another from the group consisting of methyl, ethyl, n-propyl, isopropyl, n-butyl, sec.-butyl, tert.-butyl, isobutyl, n-pentyl, n-hexyl, dodecyl, octadecyl and cyclohexyl.

3. The composition according to claim 1, wherein the substituent $R^2$ is attached to the $(R^1O)_{3-x}(R^1)_xSi—(CH_2)_n—CH_2$ moiety via a nitrogen atom.

4. The composition according to claim 1, wherein the at least one corrosion-inhibiting silane compound is selected from the group consisting of N-trimethoxysilylpropyl imidazole, 1 N-trimethoxysilylpropyl-1,2,4-triazole and 4N-trimethoxysilylpropyl-1,2,4-triazole and mixtures thereof.

5. The composition according to claim 1 further comprising additional components selected from the group consisting of nanoparticles, dyes, solvents and additives.

6. The composition according to claim 1 further comprising at least one corrosion-inhibiting non-silane compound.

7. The composition according to claim 6, wherein the at least one corrosion-inhibiting non-silane compound is microencapsulated.

8. The composition according to claim 1, wherein the at least one corrosion-inhibiting silane compound is contained in an amount of 3 to 5% by weight based on the weight of the composition.

9. A method for protecting a metal substrate against corrosion, comprising the following steps:

a. applying an anticorrosive composition comprising a sol-gel material, the sol-gel material comprising at least one corrosion-inhibiting silane compound onto a metal substrate, and b. curing the anticorrosive composition;
wherein the at least one corrosion-inhibiting silane compound has the general formula (I)

$$(R^1O)_{3-x}(R^1)_x Si-(CH_2)_n-CH_2-R^2 \quad (I),$$

in which the substituents $R^1$ may be the same or different and are selected from the group consisting of hydrogen, alkyl, acyl or aryl,
the substituent $R^2$ is a nitrogen-containing, heterocyclic moiety,
x is equal to 0, 1 or 2, and
n is an integer between 0 and 10,
wherein the substituent $R^2$ is selected from the group consisting of triazolyls, pyrazolyls, isoxazolyls, oxazolyls and thiazolyls.

10. The method according to claim 9, wherein the metal substrate is selected from magnesium, aluminum and alloys thereof.

11. The method according to claim 10, wherein the substrate is pretreated before the application of the anticorrosive composition.

12. The method according to claim 9, wherein a cover layer is additionally applied to the cured composition.

13. The method according to claim 9, wherein a primer is additionally applied to the cured composition.

14. A corrosion-resistant metal substrate comprising a metal substrate coated with an anticorrosive composition, the anticorrosive composition comprising a sol-gel material,
wherein the sol-gel material comprises at least one corrosion-inhibiting silane compound, wherein the at least one corrosion-inhibiting silane compound has the general formula (I)

$$(R^1O)_{3-x}(R^1)_x Si-(CH_2)_n-CH_2-R^2 \quad (I),$$

in which the substituents $R^1$ may be the same or different and are selected from the group consisting of hydrogen, alkyl, acyl or aryl,
the substituent $R^2$ is a nitrogen-containing, heterocyclic moiety,
x is equal to 0, 1 or 2, and
n is an integer between 0 and 10,
wherein the substituent $R^2$ is selected from the group consisting of triazolyls, pyrazolyls, isoxazolyls, oxazolyls and thiazolyls.

* * * * *

UNITED STATES PATENT AND TRADEMARK OFFICE
CERTIFICATE OF CORRECTION

| | | |
|---|---|---|
| PATENT NO. | : 8,361,627 B2 | Page 1 of 1 |
| APPLICATION NO. | : 13/145154 | |
| DATED | : January 29, 2013 | |
| INVENTOR(S) | : Theo Hack et al. | |

It is certified that error appears in the above-identified patent and that said Letters Patent is hereby corrected as shown below:

On the Title Page

Column 1, line 3 of item (75), "Vienna" should read -- Wien --.

In the Claims

Column 10, line 48, "1 N-" should read -- 1N- --.

Signed and Sealed this
Twenty-fifth Day of August, 2015

Michelle K. Lee
*Director of the United States Patent and Trademark Office*